United States Patent [19]

Convent

[11] 4,045,207
[45] Aug. 30, 1977

[54] SYNERGISTIC HERBICIDAL COMPOSITION COMPRISING N-(BUTOXYMETHYL)-6'-TERT-BUTYL-2-CHLORO-o-ACETOTOLUIDIDE AND PYRAZON

[75] Inventor: Bernard Convent, Leernes, Belgium

[73] Assignee: Monsanto Company, St. Louis, Mo.

[21] Appl. No.: 605,708

[22] Filed: Aug. 18, 1975

[51] Int. Cl.$^2$ .................. A01N 9/22; A01N 9/20; A01N 9/02
[52] U.S. Cl. .......................... 71/92; 71/76; 71/118
[58] Field of Search .................. 71/92, 118

[56] References Cited

U.S. PATENT DOCUMENTS

| 3,210,353 | 10/1965 | Reicheneder et al. | 71/92 |
| 3,442,945 | 5/1969 | Olin | 71/118 |
| 3,547,620 | 12/1970 | Olin | 71/118 |
| 3,773,492 | 11/1973 | Fischer | 71/92 |

*Primary Examiner*—Glennon H. Hollrah
*Attorney, Agent, or Firm*—William I. Andress; Donald W. Peterson

[57] ABSTRACT

A synergistic herbicidal composition comprising as the active ingredient a mixture of N-(butoxymethyl)-6'-tert-butyl-2-chloro-o-acetotoluidide and 5-amino-4-chloro-2-phenyl-3(2H)-pyridazinone and use of said composition in sugarbeets.

7 Claims, No Drawings

SYNERGISTIC HERBICIDAL COMPOSITION COMPRISING N-(BUTOXYMETHYL)-6'-TERT-BUTYL-2-CHLORO-o-ACETOTOLUIDIDE AND PYRAZON

BACKGROUND OF THE INVENTION

1. Field of the Invention

The invention herein pertains to the field of herbicides. In particular, the invention pertains to a synergistic herbicidal composition having as the active ingredient a mixture of N-(butoxymethyl)-6'-tert-butyl-2-chloro-o-acetotoluidide and 5-amino-4-chloro-2-phenyl-3(2H)-pyridazinone (common name pyrazon). The herbicidal composition herein has particular application in the control of undesired plants associated with sugarbeets.

2. Description of the Prior Art

It is known in the prior art to use various pyridazones as herbicides. A variety of chemical compounds have been admixed with various pyridazones in efforts to discover new herbicidal compositions having unique additive, antagonistic or synergistic properties with respect to different weed plants associated with various crop plants.

The particular pyridazone of interest and use herein as a component of the combination herbicide of the present invention, i.e., 5-amino-4-chloro-2-phenyl-3(2H)-pyridazinone ("pyrazon" hereafter for brevity), is a known compound having herbicidal properties. Herbicidal compositions of pyrazon are available as Pyramin® formulations.

A variety of chemical compounds have been admixed with pyrazon in efforts to discover new herbicidal compositions having unique herbicidal properties with respect to different plants. Illustrative of prior art herbicide mixtures containing pyrazon and other herbicidal compounds are those containing m-carbamyloxy carbanilates, e.g., 3-(3-methylphenylcarbamyloxy) phenyl-O-methyl carbamate (West German DS No. 1,642,216); or 2-chloro-3-(4-chlorophenyl) propionic acid methyl ester (British Pat. No. 1,224,839); or N-propyl-N-chloroethyl-2,6-dinitro-4-trifluoromethylaniline or various thio- or dithiophosphoric acid esters (U.S. Pat. No. 3,849,107) or thioalkyl carbamates (U.S. Pat. No. 3,862,832).

It is also known in the prior art to use various 2-halo-2'6'-dialkyl-N-(alkoxyalkyl) acetanilides as herbicides either individually or in combination with other herbicidal compounds. For example, U.S. Pat. No. 3,551,132 discloses the herbicidal use of 2-chloro-2',6'-diethyl-N-(methoxymethyl) acetanilide (common name alachlor) admixed with 3'-(carbamoyloxy) anilides. British Pat. No. 1,176,547 discloses the herbicidal use of a mixture of alachlor and linuron, i.e., 3-(3,4-dichlorophenyl)-1-methoxy-1-methylurea.

In still further particular, U.S. Pat. Nos. 3,442,945 and 3,547,620 both of which are also assigned to applicant's assignee, disclose a broad class of herbicidal 2-halo-2',6'-dialkyl-N-(alkoxyalkyl) acetanilides, expressly including N-(butoxymethyl)-6'-tert-butyl-2-chloro-o-acetotoluidide. This compound has tentatively been designated as "terbuchlor"; application has been made by applicant's assignee to the American Standards Institute for registration of this name as the common name for said compound. Hence, the term terbuchlor will sometimes be used hereafter in the specification for brevity. The 3,442,945 and 3,547,620 U.S. patents both disclose that the acetanilide compounds therein may be admixed with other herbicidal compounds, including certain trisubstituted ureas, halogenated phenoxy-acetic acids, salts or esters, triazines, acetamides or acetanilides, etc. However, pyrazon-type compounds are not disclosed in these patents.

To applicant's knowledge, there has been no recognition or disclosure in the prior art of a herbicidal composition comprising terbuchlor and a pyridazone of the type including pyrazon, which together impart complementary, supplementary and/or synergistic action with respect, particularly, to undesirable vegetation associated with sugarbeets.

The phenomenon of synergism is well known to those skilled in the art and, in the herbicidal art, relates to herbicidal compositions of mixed components whose total herbicidal effect is unexpectedly greater than the additive effect of the individual components on particular plants or a spectrum of plants. The use of synergistic mixtures for the control of plant growth permits the utilization of a lesser total amount of herbicidal composition and/or lesser quantities of individual components in the composition to obtain the same or improved results than are obtained when a greater amount of herbicidal composition containing only the individual components or additive mixtures thereof. The use of lesser quantities of active ingredients in a herbicidal composition may also increase the margin of crop safety in the use of those active ingredients.

The concepts of synergism and antagonism (i.e., negative, neutralizing or nullifying effect of one component on another component) in herbicidal combinations have been reduced to mathematical formulation and graphical representation by some authors. For example, by the method described by S. R. Colby in "Weeds," Vol. 15, No. 1 (1967) pages 20–22, the expected response of a combination of herbicides is obtained by taking the product of the percent-of-control values for the individual herbicides and dividing by $(100)^{n-1}$ where $n$ is the number of herbicides in the combination.

Another method of expressing synergism and antagonism is described by P. M. L. Tammes in "Netherlands Journal of Plant Pathology," 70 (1964), 73–80. By the Tammes method, a graphic representation is given of the effect of mixtures of herbicides. Each of the components is expressed as a coordinate on a graph and a quantitatively defined effect, e.g., a percent plant mortality, e.g., 50%, 85%, etc., is inserted in the graph. These values are obtained by interpolation. The line which connects the points is called an "isobole." With an isobole the effect of different proportions of the individual components can be evaluated. The Tammes isoboles method has proven reliable in evaluating the synergistic effect of the herbicidal composition of this invention.

As used herein the term "active ingredient" denotes a mixture of terbuchlor and pyrazon having the combined supplementary, complementary and synergistic properties unique to this mixture.

The term "plant" as used herein encompasses dormant seeds, germinant seeds, germinative seeds, emerging seedlings and established vegetation including roots and above-ground portions.

The term "control" as used herein is inclusive of the effects of killing, inhibiting the growth, reproduction or proliferation and removing, destroying or otherwise diminishing the occurrence or activity of plants and is applicable to any of the stated effects or combinations thereof.

SUMMARY OF THE INVENTION

The present invention relates to a synergistic herbicidal composition containing as the active ingredient therein a mixture of terbuchlor and pyrazon as above defined, and to the herbicidal use of such compositions particularly useful in sugarbeets, to control undesired plants such as Chenopodium album, Polygonium lapathifolium, Polygonium persicaria, Digitaria sanguinalis, Solanum nigrum, Sinapis arvenis, Stellaria media, Alopecurus myosuroides and Matricaria chamomilla.

DESCRIPTION OF PREFERRED EMBODIMENTS

EXAMPLE observed approximately 3 weeks after sowing and the results recorded.

In the table below, the various plant species tested are identified according to the following abbreviations:

| | |
|---|---|
| Chen. alb. | Chenopodium album |
| Pol. lap. | Polygonum lapathifolium |
| Pol. per. | Polygonum persicaria |
| Sin. arv. | Sinapis arvensis |
| Stel. med. | Stellaria media |
| Alop. myos. | Alopecurus myosuroides |
| Matric. cham. | Matricaria chamomilla |
| Dig. sang. | Digitaria sanguinalis |
| Sol. nigr. | Solanum nigrum |

A dash or blank space signifies that no data is available. In some instances the numerical values were distorted by fungus infestation, particularly in situations where more than 2.0 kg/ha of pyrazon were used.

Table I

| Active Ingredient | Rate Kg/ha | Percent Control of Plants | | | | | | | | | |
|---|---|---|---|---|---|---|---|---|---|---|---|
| | | Sugar Beets | Chen. alb. | Pol. per. | Pol. lap. | Dig. san. | Sin. arv. | Stel. med. | Sol. nig. | Alop. myos. | Matric. cham. |
| Terbuchlor | 4 | 45 | 85 | 90 | — | 100 | 70 | 90 | 90 | 100 | 99 (2) |
| | 2 | 30 | 60 | 45 | — | 100 | 50 | 85 | 85 | 95 | 90 (2) |
| | 1 | 12 | 55 | 10 (2) | 60 (2) | 100 | 40 | 78 | 83 | 88 | 95 (1) |
| | 0.5 | 5 | 25 | 0 (2) | 35 (2) | 99 | 60 (2) | 38 | 70 | 75 | 80 (1) |
| | 0.25 | 0 | 30 | — | 25 | 99 | 0 | 20 | 50 | 35 | 50 (2) |
| | 0.125 | 0 | 10 | — | 0 | 95 | 0 | 20 | 25 | 15 | 25 (2) |
| Pyrazon | 4 | 0 | 90 | — | 85 | 70 | 85 | 85 | 85 | 60 | 99 (2) |
| | 2 | 0 | 85 | — | 65 | 45 | 80 | 65 | 75 | 20 | 99 (2) |
| | 1 | 0 | 60 | 75 (2) | 25 (2) | 38 | 40 | 15 | 40 (2) | 10 | 100 (1) |
| | 0.5 | 0 | 80 | — | 0 | 30 | — | 50 | 40 | 0 | 99 (2) |

| Active Ingredient | Rate Kg/ha(3) | Sugar Beets | Chen. alb. | Pol. per. | Pol. lap. | Dig. san. | Sin arv. | Stel med. | Sol nigr. | Alop. myos. | Matric cham. |
|---|---|---|---|---|---|---|---|---|---|---|---|
| Terbuchlor and Pyrazon | 2 + 1 | 30 | 95 | 85 | — | 100 | 90 | 100 | 95 | 85 | 100 (2) |
| | 1 + 1 | 15 | 99 | 80 | — | 100 | 95 | 95 | 90 | 85 | 100 (2) |
| | 0.5 + 2 | 12 (1) | 90 | — | 90 | 99 | — | — | — | 90 | 100 (2) |
| | 0.5 + 1 | 2 | 90 | 40 (2) | 85 (2) | 100 | 100 (2) | 90 (2) | 85 | 85 | 100 (1) |
| | 0.5 + 0.5 | 5 | 85 | — | 30 | 99 | — | 85 | 85 | 75 | 100 (2) |
| | 0.25 + 2 | 0 | 100 | — | 85 | 99 | — | 95 | 95 | 85 | 100 (2) |
| | 0.25 + 1 | 5 | 99 | — | 85 | 99 | 50 | 85 | 85 | 85 | 100 (2) |
| | 0.25 + 0.5 | 0 | 90 | — | 20 | 99 | 40 | 50 | 65 | 95 | 99 (2) |
| | 0.125 + 2 | 0 | 90 | — | 85 | 100 | — | 85 | 80 | 40 | 100 (2) |
| | 0.125 + 1 | 0 | 80 | — | 35 | 99 | 30 | 60 | 60 | 20 | 100 (2) |
| | 0.125 + 0.5 | 0 | 80 | — | 20 | 99 | 0 | 10 | 40 | 20 | 99 (2) |

(1) Percent averages for four replications
(2) Percent averages for two replications
(3) Numbers in the first column refer to terbuchlor rates.

Terbuchlor may be prepared by methods generally known to the art. For example, in Example 4 of each of the above-cited U.S. Pat. Nos. 3,442,945 and 3,547,620, terbuchlor is prepared by reacting 2-tert-butyl-6-methyl-N-methyleneaniline and chloroacetyl chloride with n-butanol according to conditions noted in the example.

Pyrazon also may be prepared by known methods commonly used to prepare pyridazones. Also, as indicated above, herbicidal formulations of pyrazon are available as Pyramin® formulations.

Terbuchlor and pyrazon were tank mixed and applied to the surface of a sandy loam soil contained in plastic pots and previously sown with crop and weed seeds at 1 cm depth. Application of the mixed herbicide was made at a volume equivalent of 4000 l/ha with a Devilbiss atomizer No. 152. Initial irrigation of 1 mm was applied by overhead means and subsequent watering requirements by subirrigation. The plants were visually The synergistic response for terbuchlor/pyrazon herbicidal mixtures is well shown by data in Table 1. Thus, consider the average rates of the three herbicides, i.e., terbuchlor, pyrazon and a mixture of the two, required to control 85% of the weeds ($GR_{85}$), and the average maximum rates of the herbicides for 15% or less growth reduction ($GR_{15}$) of the crop plants for illustrative purposes.

For example, in order to control Chen. alb. ($GR_{85}$) 4 kg/ha of terbuchlor alone is required; however, such rates is not selective for use with sugarbeets which are severely injured. Similarly, 2 kg/ha of pyrazon is required for a $GR_{85}$, without injury to the crop plants. In contrast, terbuchlor/pyrazon mixtures of either 0.125 + >1.0, 0.25 + <0.5, 0.5 + 0.5, 1.0 + <1.0 or 1.0 + <2.0 kg/ha will selectively control Chen. alb. in sugarbeets. In addition, it will be noted that various combinations of terbuchlor/pyrazon mixtures also control all other weed species listed in Table 1.

Further, whereas it requires 4.0 kg/ha of pyrazon and 2.0 kg/ha of terbuchlor individually to control *Stel. med.*, (with no selectivity to sugarbeets as regards terbuchlor), this weed is selectively controlled in sugarbeets by 0.125 + 2.0, 0.25 + 1.0, 0.5 + 0.5, 1.0 + <1.0 and 1.0 + <2.0 kg/ha terbuchlor/pyrazon combinations. Again, these combinations are also effective against the other weeds listed in Table 1.

Further synergism of the combination herbicide of this invention is shown with respect to *Sin arv.*, which when treated with each chemical individually, requires substantially more than 4.0 kg/ha of terbuchlor and at least 4.0 kg/ha of pyrazon for control, with no safety whatever in sugarbeets as regards terbuchlor above 1.0 kg/ha. However, *Sin. arv.* is selectively controlled with as little as 0.5 + <1.0, 1.0 + <1.0 and 2.0 + <1.0 kg/ha terbuchlor/pyrazon mixtures. Application rates of these mixtures to control *Sin. arv.* are also adequate to control other weeds in Table 1 in sugarbeets.

Similarly, about 2.0 and 4.0 kg/ha of terbuchlor and pyrazon, respectively, are required to control *Sol. nigr.* when separately applied. However, this weed is effectively controlled with safety in sugarbeets with 0.25 + 1.0, 0.5 + 0.5 and 1.0 + <1.0 kg/ha terbuchlor/pyrazon mixtures.

A Tammes isobole graphic representation of the synergistic effect of terbuchlor/pyrazon combinations would show on a coordinate graph the concentration in kg/ha required to achieve $GR_{85}$, for example, with pyrazon rates shown along the ordinate (horizontal axis) and terbuchlor rates shown along the abscissa (vertical axis). A line is then drawn to join the $GR_{85}$ rates for each compound; this line is the additive isobole for the mixture. Then holding one of the component rates constant while varying the rate of the other component, data points for each $GR_{85}$ rate are fixed on the graph. Any combination of weight ratios falling inside (or under) the additive isobole and having a $GR_{85}$ rate for weeds should exhibit synergism, and the corresponding interpolated curve is termed the synergistic isobole. Combinations having $GR_{85}$ data points falling outside (or above) the additive isobole should exhibit antagonism and the corresponding interpolated curve is termed the antagonistic isobole. Data points falling on the additive isobole line itself represent mixtures whose combined components have only additive effects. If a particular herbicidal combination has a $GR_{85}$ rate for weeds within the area under the additive isobole for that combination, but the data also exhibits injury to the crop greater than 15% at that rate, obviously, the herbicidal combination may not be selective for use in that particular crop under the specific test conditions.

In specific applications of the Tammes isoboles method, data derived from Table 1 is tabulated in Tables 2 and 3 showing the application rates (in kg/ha) for the individual components terbuchlor and pyrazon and various concentration ratios of each in mixtures thereof required to achieve $GR_{85}$ for the specific weeds *Chenopodium album* and *Stellaria media*, respectively. Data points for the $GR_{85}$ rates are fixed on the graph below the additive isobole and a line of best fit is drawn through the data points to derive a curve termed the "interpolative synergistic isobole."

Table 2

*Chenopodium album*
$GR_{85}$ Rates (Kg/Ha)

| Terbuchlor | |
|---|---|
| 4.0 | |

| Pyrazon | |
|---|---|
| 2.0 | |

| Terbuchlor | + | Pyrazon |
|---|---|---|
| 0.125 | | 1.5 |
| 0.25 | | <0.5 |
| 0.5 | | 0.5 |
| 1.0 | | <1.0 |
| 2.0 | | <1.0 |

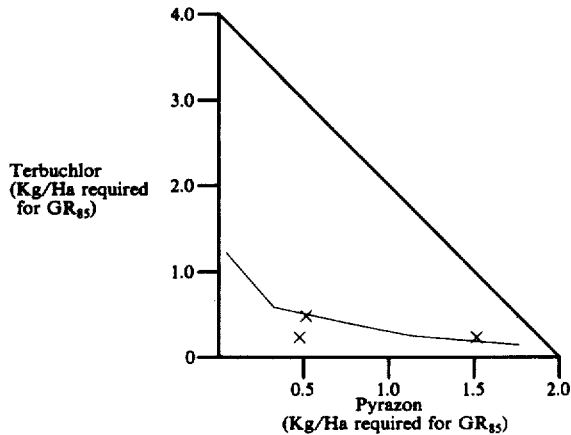

Table 3

*Stellaria media*
$GR_{85}$ Rates (Kg/Ha)

| Terbuchlor | |
|---|---|
| 2.0 | |

| Pyrazon | |
|---|---|
| 4.0 | |

| Terbuchlor | + | Pyrazon |
|---|---|---|
| 0.125 | | 2.0 |
| 0.25 | | 1.0 |
| 0.5 | | 0.5 |
| 1.0 | | <1.0 |
| 2.0 | | <1.0 |

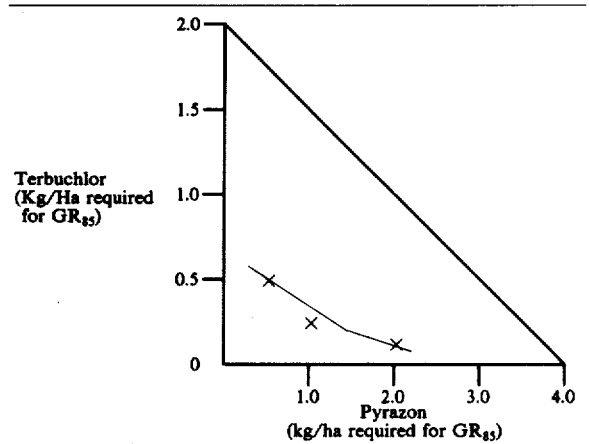

The active ingredient herein can be admixed with one or more adjuvants which can be solid or liquid extenders, carriers, diluents, conditioning agents and the like to form herbicidal compositions. Herbicidal compositions containing the active ingredients of this invention can be formulated with or in the form of granules, wettable powders, aqueous suspensions, dust formulations, emulsifiable oils and solutions in solvents. In general, these formulations can all contain one or more surface-active agents.

Surface-active agents which can be used in herbicidal formulations are well known to those skilled in the art and have been well documented in patents, bulletins and textbooks.

The preparation, formulations and particle size of the granules, wettable powders, aqueous suspensions, dusts, emulsifiable oils and solutions in solvents are also well known to those skilled in the art and well documented.

The active ingredient is usually present in the herbicidal compositions in a range of about 0.5 to 95 parts by weight per 100 parts by weight of wettable powder and dust formulations and from about 5 to 95 parts by weight per 100 parts by weight emulsifiable oil formulations. Formulations containing more or less than the above quantities of active ingredient can easily be prepared by those skilled in the art.

The quantity of active ingredient to be used in the field may vary within certain limits depending upon variables known to those in the art, e.g., condition of the soil, climate, plant, etc. In general, however, amounts ranging from about 0.05 to 6.0 or more kg/ha should be adequate; a preferred range being from about 0.125 to 4.0 kg/ha or suitably, an amount within the range of from 0.250 to 2.0 kg/ha. Terbuchlor/pyrazon ratios may vary within fairly wide limits, e.g., from 1:8 to 8:1, a preferred ratio being within the range of from 1:4 to 4:1 or even 1:2 to 2:1. Preliminary experience with pyrazon indicates that above about two or more kg/ha, either alone or in combination with terbuchlor, pyrazon has a tendency to render some plants susceptible to fungal infection.

Modes of application of the herbicidal compositions of this invention to the plant are well-known to those skilled in the art. The application of liquid and particulate solid herbicidal formulations to the above-ground portions of plants can be carried out by conventional methods, e.g., power dusters, boom and hand sprayers and spray dusters. Although in more practical and recommended usage, the herbicidal compositions herein should be applied simultaneously as conjugate components in a mixture. However, it is within the purview of this invention to apply the individual components sequentially in either order, the time interval between successive applications being such as to accomplish the object of this invention, i.e., the supplementary/complementary/synergistic effects of terbuchlor/pyrazon combination.

While the illustrative embodiments of the invention have been described hereinbefore with particularity, it will be understood that various other modifications will be apparent to and can readily be made by those skilled in the art without departing from the scope and spirit of the invention. Accordingly, it is not intended that the scope of the claims appended hereto be limited to the examples and description set forth herein but rather the claims be construed as encompassing all the features of patentable novelty which reside in the present invention including all features which would be treated as equivalents thereof by those skilled in the art to which the invention pertains.

I claim:

1. A herbicidal composition consisting essentially of a herbicidally effective amount of a mixture of (a) N-(butoxymethyl)-6'-tert-butyl-2-chloro-o-acetotoluidide and (b) 5-amino-4-chloro-2-phenyl-3(2H)-pyridazinone wherein the ratio of (a) to (b) is within the range of from about 1:8 to 4:1 and an inert carrier therefore.

2. Composition according to claim 1 wherein components (a) and (b) together comprise from about 0.5 to 95% by weight of said composition, the balance comprising adjuvant.

3. Composition according to claim 2 wherein the ratio of (a) to (b) is within the range of from about 1:4 to 4:1.

4. A method for controlling undesirable plants associated with sugarbeets which comprises applying to the locus of said plants a herbicidally effective amount of a mixture of (a) N-(butoxymethyl)-6'-tert-butyl-2-chloro-o-acetotoluidide and (b) 5-amino-4-chloro-2-phenyl-3(2H)-pyridazinone wherein the ratio of (a) to (b) is within the range of from about 1:8 to 4:1.

5. Method according to claim 4 wherein said mixture is applied at a rate within the range of from about 0.625 to 2.0 kg/ha.

6. Method according to claim 5 wherein the ratio of (a) to (b) is within the range of from about 1:4 to 4:1.

7. Method according to claim 5 wherein said mixture is applied at a rate within the range of from about 0.125 to 4.0 kg/ha.

* * * * *